(12) United States Patent
Rowe et al.

(10) Patent No.: US 7,245,957 B2
(45) Date of Patent: Jul. 17, 2007

(54) SNAP ELECTRODE

(75) Inventors: Chuck Rowe, Wabasha, MN (US); Timothy R. Kretschmer, Wabasha, MN (US)

(73) Assignee: Tyco Healthcare Group LP, Mansfield, MA (US)

( * ) Notice: Subject to any disclaimer, the term of this patent is extended or adjusted under 35 U.S.C. 154(b) by 0 days.

(21) Appl. No.: 10/946,673

(22) Filed: Sep. 22, 2004

(65) Prior Publication Data

US 2005/0101853 A1 May 12, 2005

Related U.S. Application Data

(60) Provisional application No. 60/519,322, filed on Nov. 12, 2003.

(51) Int. Cl.
*A61B 5/04* (2006.01)

(52) U.S. Cl. .................. 600/391; 600/392; 600/394

(58) Field of Classification Search ........... 600/372, 600/386, 391, 392, 394; 607/149, 152, 153
See application file for complete search history.

(56) References Cited

U.S. PATENT DOCUMENTS

| 3,993,049 A | 11/1976 | Kater |
| 4,267,840 A | 5/1981 | Lazar et al. |
| 4,526,176 A | 7/1985 | Bremer et al. ............ 128/641 |
| 4,554,924 A | 11/1985 | Engel ........................ 128/640 |
| 4,617,935 A | 10/1986 | Cartmell et al. ........... 128/641 |
| 4,727,881 A | 3/1988 | Craighead et al. |
| 5,406,945 A | 4/1995 | Riazzi et al. .............. 128/641 |
| 5,511,548 A | 4/1996 | Riazzi et al. .............. 128/641 |
| 6,745,082 B2 * | 6/2004 | Axelgaard .................. 607/142 |
| 2005/0015134 A1 * | 1/2005 | Carim ....................... 607/142 |

FOREIGN PATENT DOCUMENTS

EP 0884021 * 12/1998

* cited by examiner

*Primary Examiner*—Lee S. Cohen
(74) *Attorney, Agent, or Firm*—Lawrence A. Chaletsky; Elizabeth A. O'Brien (57) ABSTRACT

A medical snap electrode having a conductive tape portion disposed between the cover material and conduction layer of the electrode. The conductive tape portion becomes part of an electrical connection from a top snap, positioned above the cover material, to the conductive tape then to the conductive layer. The conductive tape includes conductive adhesive on at least one of its surfaces and thereby provides a more robust electrical connection from a top snap to a conductive layer in the electrode and ultimately to a subject's skin. Viewing of the snap through the conductive film layer is prevented. The conductive tape thus provides an improved conduction path for distributing electrical current from the top snap to a subject's skin in addition to the conduction path through bottom snap. The improved conduction path can prevent heating or apprehension of potential heating by a subject or clinician.

18 Claims, 7 Drawing Sheets

SNAP ELECTRODE

This Application claims the benefit of U.S. Provisional Patent Application No. 60/519,322 filed on Nov. 12, 2003, which is hereby incorporated by reference in its entirety.

BACKGROUND OF THE INVENTION

1. Technical Field

The present disclosure relates to a biomedical snap electrode and method of manufacturing a biomedical snap electrode for delivering electrical current to a subject. More particularly, a biomedical snap electrode and method of manufacturing a biomedical snap electrode for electrical stimulation of muscle tissue or nerves is disclosed.

2. Description of the Related Art

Medical snap electrodes are well known in the medical field for use in measuring and monitoring the condition of a subject by interpreting various types of electrical signals monitored through the skin of the subject. Some well known applications which use medical snap electrodes include electrocardiography and electroencephalography. In those applications small signals are received though electrodes that are attached to the subject's skin. A lead wire provides a connection between the electrode and the monitoring equipment, which amplifies and displays or interprets the small signal.

Other well known applications of snap electrodes include electrical muscle stimulation (EMS), transcutaneous electrical nerve stimulation (TENS) and biofeedback. In EMS and TENS applications, for example, electrical current is applied through the skin to stimulate a subject's muscles for therapeutic purposes or nerves for pain reduction purposes and for physical training.

Figure 1:
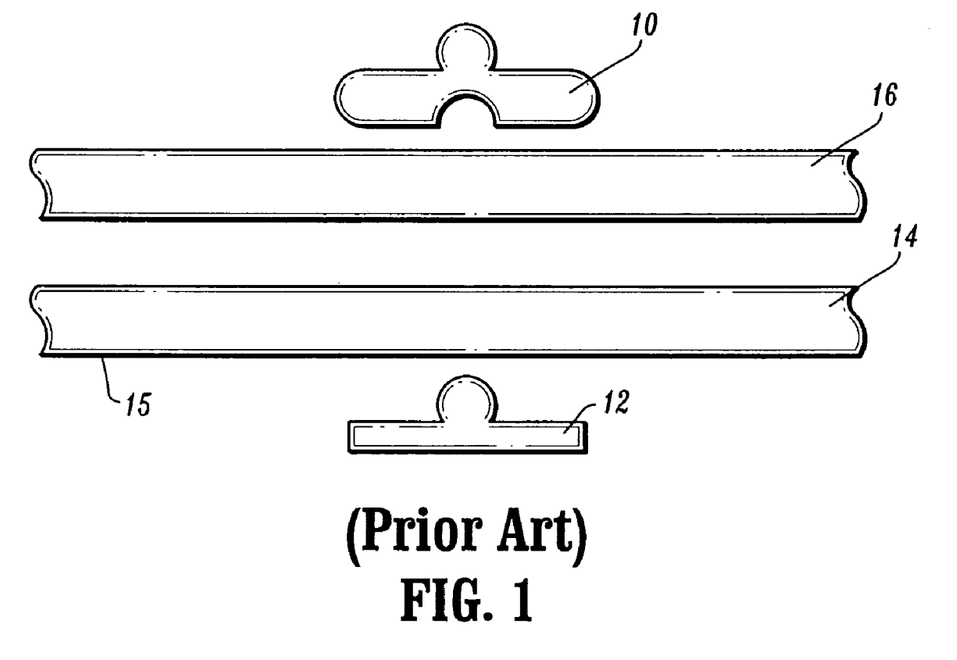
FIG. 1 is a schematic cross sectional view illustrating a construction method for snap electrodes according to the prior art.

One commonly used method for fabricating a snap electrode by attaching a snap assembly into a stimulating electrode is described with reference to FIG. 1. A conductive top snap 10 and a conductive bottom snap 12 designed to mate with the top snap 10 are pressed together to secure the bottom snap 12 against a conductive layer 14 and to secure the top snap 10 against a cover layer 16 on the electrode. The conductive top snap 10 is typically made from metal and the conductive bottom snap 12 is typically made from metal or plastic with a conductive layer deposited thereon. The conductive layer 14 can be a conductive film or a layer of thin metal such as aluminum or tin, for example. The cover layer is typically made from a non-conductive material such as polypropylenes, polyethylene, polyurethane or other flexible material.

When the top snap 10 and bottom snap 12 are pressed together, portions of the bottom snap 12 make electrical contact with portions of the top snap 10 by at least partially penetrating the conducive layer 14 and the cover layer 16. An electrical connection is thereby made between the bottom and top snap. The electrical current flow for an electrode using this construction follows a path from a stimulating device (not shown) to a lead wire (not shown) to the top snap 10 to the bottom snap 12 and then to the conductive layer 14. A conductive gel (not shown) is usually applied to the bottom surface 15 of the conductive layer 14 to improve electrical contact with an area of a subject's skin.

Figure 2:
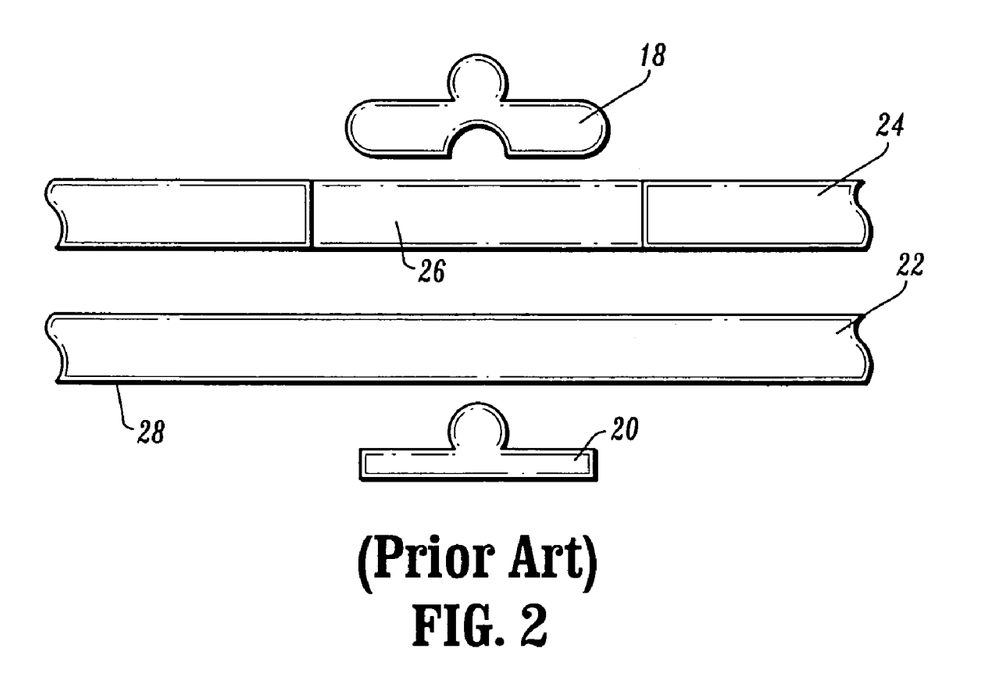
FIG. 2 is a schematic cross sectional view illustrating an alternative construction method for a snap electrode according to the prior art.

Another commonly used method for fabricating a snap electrode is described with reference to FIG. 2. A conductive top snap 18 and a non-conductive bottom snap 20 designed to mate with the top snap 18 are pressed together to secure the bottom snap 20 against a conductive layer 22 and to secure the top snap 18 against a cover layer 24 on the electrode. The conductive top snap 18 is typically made from metal and the non-conductive bottom snap 20 is typically made from plastic. The conductive layer 22 is typically a conductive film or a layer of thin metal such as aluminum or tin. The cover layer 24 is typically made from a non-conductive material such as polypropylenes, polyethylene, polyurethane or other flexible material.

In snap electrodes that are assembled using the method described with reference to FIG. 2, an opening 26 larger than the snap is cut through the cover layer 24 to allow the top snap 18 to rest directly on the conductive layer 22. The electrical current flow for an electrode using this construction follows a path from a stimulating device (not shown) to a lead wire (not shown) to the top snap 18 to the conductive layer 22. A conductive gel (not shown) is typically applied to the bottom surface 28 of the conductive layer 22 to improve electrical contact with an area of a subject's skin.

In some cases, applications of electrical energy to a subject for EMS and/or measurement of electrical signals causes some apprehension due to the subject's perception that the electrode can burn or otherwise cause discomfort to the subject. Such apprehension can be enhanced when a snap connector is visible by viewing the bottom surface of an electrode which contact's the subject's skin. Each of the commonly used methods of constructing electrodes described above with reference to FIG. 1 and FIG. 2 include visible snaps on their bottom surface. Even though any substantial heating of the electrode or snaps is highly unlikely, it can be envisioned that a defective conductive layer could potentially cause a hot spot touching the patient's of the skin. Accordingly, many patients and/or practitioners avoid use of appropriate medical electrodes. It would therefore be desirable to provide a medical snap electrode that prevents viewing of a snap through the conductive layer of the electrode to reduce apprehension of burning or discomfort.

SUMMARY OF THE INVENTION

The present invention provides a medical snap electrode having a conductive tape portion disposed between the cover material and conductive layer of the electrode. The conductive tape portion becomes part of an electrical connection from a top snap positioned above (proximal to) the cover material to the conductive tape then to the conductive layer. The conductive tape includes conductive adhesive on at least one of its surfaces and thereby provides a more robust electrical connection from a top snap to a conductive layer in the electrode and ultimately to a subject's skin.

In the discussion that follows, the term "proximal" refers to a portion of a structure that is closer to a clinician, and the term "distal" refers to a portion that is further from the clinician. As used herein, the term "subject" refers to a patient that receives or uses the electrode according to the present disclosure. In the present disclosure, the term "clinician" refers to an individual administering therapy, installing or using the electrode according to the present disclosure on a patient.

The present invention allows the bottom snap to be made from a non-conductive material and to be positioned on the top surface of the conductive layer to prevent viewing of the snap through the electrode's bottom surface. If a conductive bottom snap is used, the conductive tape can be pressed between the bottom and top snaps to provide a more robust connection there-between. The separate conduction path and placement of the bottom snap away from the subject's skin also reduces apprehension by a clinician or subject of potential heating of the electrode where it contacts the subject's skin.

An illustrative embodiment of the invention provides a snap electrode including a conductive layer having a proximal surface and a distal surface. A cover layer having a proximal surface and distal surface is disposed over the conductive layer and substantially coextensive therewith. Conductive tape is disposed between the cover layer and the conductive layer such that the conductive tape is in electrical contact with the conductive layer. At least one conductive snap is in electrical contact with the conductive tape.

In one embodiment, a conductive bottom snap is disposed between the conductive tape and the bottom layer. The conductive bottom snap can include a top portion that extends through the cover layer. The conductive tape can include an aperture aligned with the bottom snap and the cover layer can include an aperture aligned with the bottom snap such that the bottom snap is accessible for attachment of a lead wire through the cover layer. In one embodiment, the bottom snap includes a top portion which extends through the aperture in the cover layer.

Another illustrative embodiment of the snap electrode according to the present disclosure includes a bottom snap disposed between the conductive tape and conductive layer. A conductive top snap is disposed on the proximal surface of the cover layer and mechanically engaged with the bottom snap. The conductive tape is disposed between the bottom snap and the top snap. A portion of the conductive tape can be pinched between mating portions of the conductive top snap and the bottom snap. In another embodiment the conductive tape can include an aperture aligned with the bottom snap. The cover layer can also include an aperture aligned with the bottom snap.

In exemplary embodiment of a snap electrode according to the present disclosure, the conductive tape has a proximal surface with a conductive adhesive disposed thereon and a distal surface with a conductive adhesive disposed thereon. The cover layer can also include a conductive adhesive disposed on its distal surface.

In the various embodiments of the snap electrode according to the present disclosure, the snap includes a conductive gel layer disposed on the distal surface of the conductive layer. A release layer is provided covering the gel layer such that the gel layer is disposed between the conductive layer and the release layer.

A particular embodiment of the snap electrode according to the present disclosure includes a conductive layer having a proximal surface and a distal surface. A cover layer having a proximal surface and distal surface is disposed over the conductive layer and is substantially coextensive therewith. The cover layer of the particular embodiment has a conductive adhesive disposed on the distal surface. In certain embodiments of the snap electrode according to the present disclosure, the snaps are not viewable through the distal surface of the conductive layer.

In the particular embodiment, conductive tape is disposed between the cover layer and the conductive layer such that the conductive tape is in electrical contact with the conductive layer. The conductive tape has a proximal surface with conductive adhesive disposed thereon and a distal surface with conductive adhesive disposed thereon. A bottom snap is disposed between the conductive tape and the conductive layer. A conductive top snap is disposed on the proximal surface of the cover layer and mechanically engaged with the bottom snap. The conductive tape is disposed between the bottom snap and the top snap. A conductive gel layer is disposed on the distal surface of the conductive layer. A release layer covers the gel layer such that the gel layer is disposed between the conductive layer and the release layer.

In various embodiments of the snap electrode according to the present disclosure, at least one snap can be made from stainless steel or nickel plated brass or other conductive materials. The cover layer can be made from foam, spun poly, tricot, polypropylene, polyethylene, or polyurethane and includes a pressure sensitive adhesive on its distal surface, for example. The conductive layer can be made from aluminum, tin, plain conductive film, conductive film coated with an aluminum layer, conductive film coated with a silver layer or conductive film coated with a silver chloride layer or the like.

The present disclosure also provides a method of constructing a snap electrode which includes the steps of assembling a conductive tape between a cover layer and a conductive layer and assembling at least one conductive snap in electrical contact with the conductive tape. The method can also include the steps of assembling a bottom snap between the conductive tape and the conductive layer and assembling a conductive top snap to the bottom snap such that the cover layer and conductive tape are disposed therebetween.

Other features, objects and advantages of the present invention are stated in or apparent from detailed descriptions of presently preferred embodiments of the invention found hereinbelow.

BRIEF DESCRIPTION OF THE DRAWINGS

The objects and features of the present disclosure, which are believed to be novel, are set forth with particularity in the appended claims. The present disclosure, both as to its organization and manner of operation, together with further objectives and advantages, may be best understood by reference to the following description, taken in connection with the accompanying drawings, wherein:

DETAILED DESCRIPTION OF THE EXEMPLARY EMBODIMENTS

The exemplary embodiments of the apparatus and method disclosed herein are discussed in terms of medical snap type electrodes, and more particularly in terms of medical snap electrodes for delivering electrical stimulation to muscle tissue or nerves. It is contemplated that the medical snap type electrode and method disclosed herein may also be used in any manner for which a medical electrode is used including, defibrillation, electrocardiography, electroencephalography and the like.

The following discussion includes a description of the medical snap electrode in accordance with the present disclosure. Reference will be made in detail to exemplary embodiments of the disclosure, which are illustrated in the accompanying figures.

Figure 3:
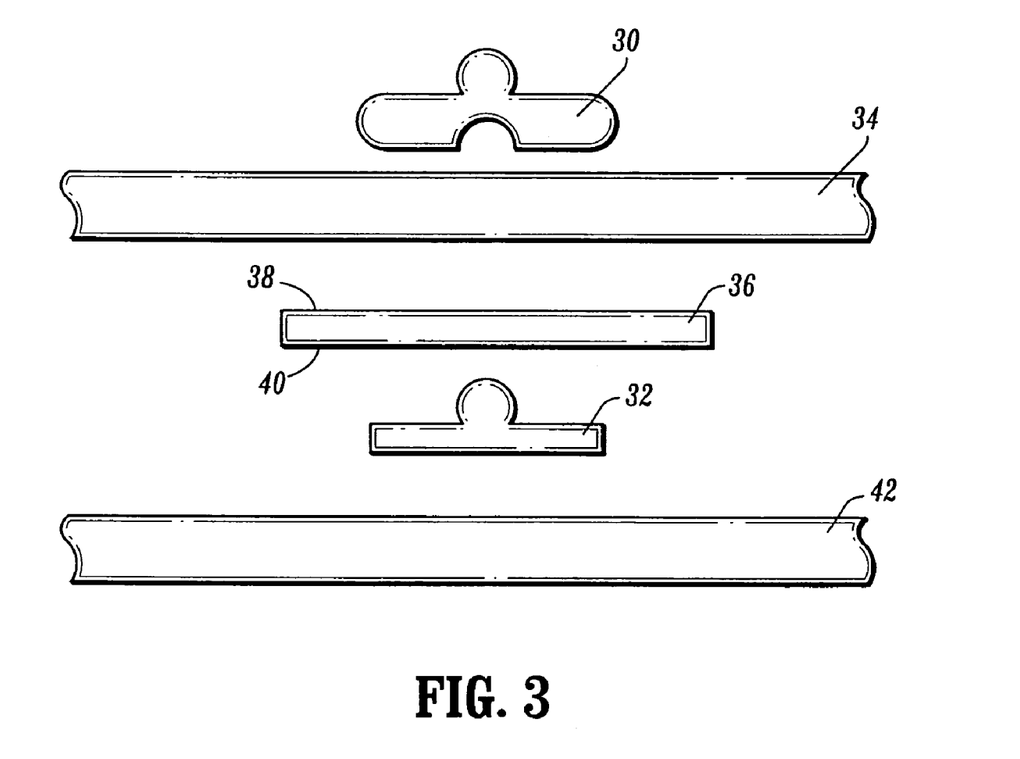
FIG. 3 is a schematic cross sectional view illustrating a construction method for a snap electrode according to an illustrative embodiment of the present invention.

Turning now to the figures wherein like components are designated by like reference numerals throughout the several views, an illustrative embodiment of the snap type medical electrode according to the present invention is described first with reference to FIG. 3. A conductive top snap 30 and a conductive bottom snap 32 designed to mate with the top snap 30 are disposed on each side of a cover layer 34 and aligned to be pressed together. Mating of the top snap 30 to the bottom snap 32 secures the top snap 30 against the cover layer 34 of the electrode. A length of conductive tape 36 sufficient to cover and overlap the bottom snap 32 is disposed between the bottom snap 32 and cover layer 34. A conductive layer 42 substantially coextensive with the cover layer 34 is disposed below (distal to) the conductive tape 36 and bottom snap 32. The double sided conductive tape 36 attaches the cover layer 34 to the conductive layer 42 and attaches the bottom snap 32 to the conductive layer 42.

When the top snap 30 and bottom snap 32 are pressed together, portions of the bottom snap 32 and conductive tape 36 make electrical contact with portions of the top snap 30 by at least partially penetrating the cover layer 34. An electrical connection is made between the bottom snap 32 and top snap 30 and between the top snap 30 and the conductive tape 36. The electrical current flow for an electrode using this construction follows a path from a stimulating device (not shown) to a lead wire (not shown) to the top snap 30 to the conductive tape 36 and bottom snap 32 to the conductive layer 42.

Figure 4:
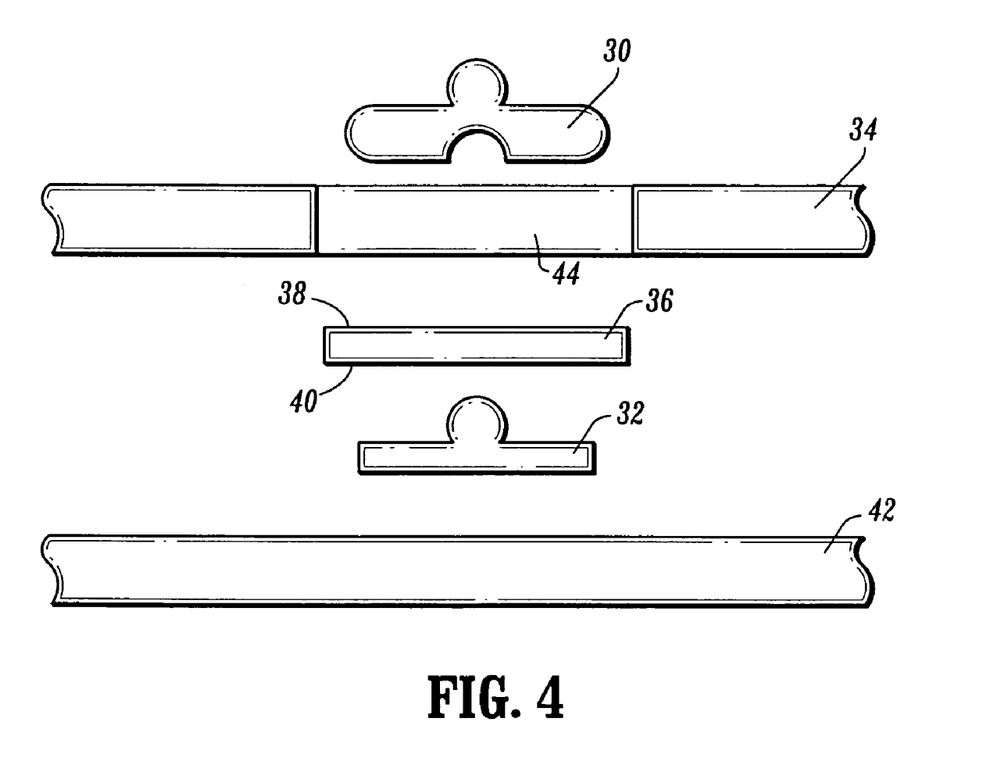
FIG. 4 is a schematic cross sectional view illustrating a construction method for snap electrode according to an alternative illustrative embodiment of the present invention.

An alternative embodiment of the present invention is described with reference to FIG. 4 in which a conductive top snap 30 and a conductive bottom snap 32 designed to mate with the top snap 30 are disposed on each side of a cover layer 34 and aligned to be pressed together. Mating of the top snap 30 to the bottom snap 32 secures the top snap 30 against the cover layer 34 of the electrode. A length of conductive tape 36 sufficient to cover and overlap the bottom snap 32 is disposed between the bottom snap 32 and cover layer 34. A conductive layer 42 substantially coextensive with the cover layer 34 is disposed below (distal to) the conductive tape 36 and bottom snap 32. The double sided conductive tape 36 attaches the cover layer 34 to the conductive layer 42 and attaches the bottom snap 32 to the conductive layer 42. In this embodiment, an aperture 44 is provided in the cover layer 34 so that the bottom snap can 32 be pressed into the top snap 30 without having to penetrate material of the cover layer 34. In a particular embodiment, the aperture 44 is larger than the top snap. The aperture 44 also allows a larger surface of the tape 36 and or bottom snap 32 to contact the top snap 30 and thereby provides an improved electrical connection therebetween.

Figure 5:
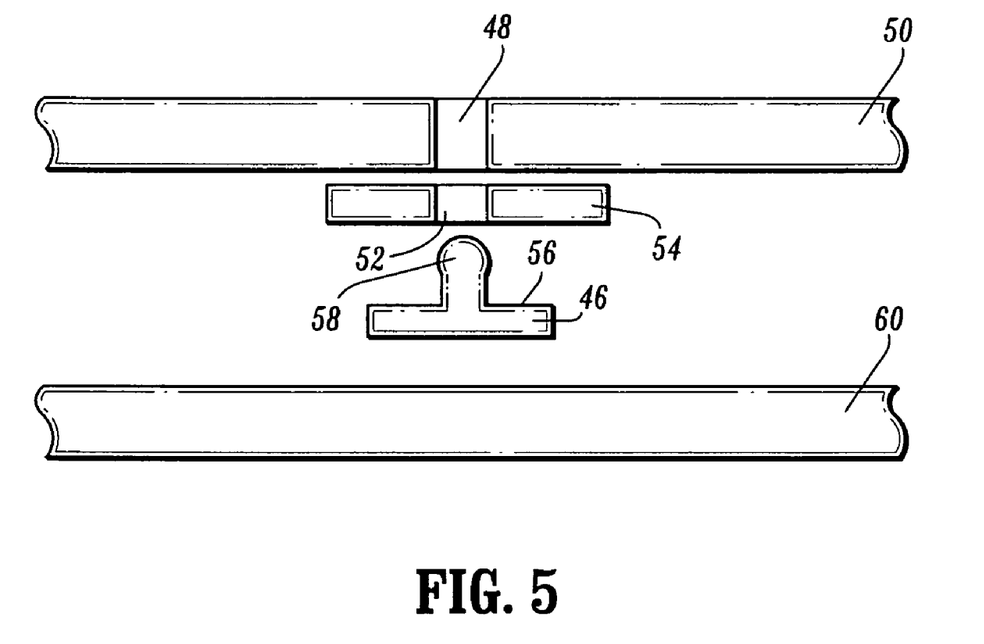
FIG. 5 is a schematic cross sectional view illustrating a construction method for a snap electrode according to a further alternative embodiment of the present invention.

Another alternative embodiment of the present invention is described with reference to FIG. 5, wherein a snap electrode and method of manufacture includes a single snap 46. A length of conductive tape 54 sufficient to cover and overlap the snap 46 is disposed between the snap 46 and cover layer 50. A conductive layer 60 substantially coextensive with the cover layer 50 is disposed below (distal to) the conductive tape 54 and snap 46. The double sided conductive tape 54 attaches the cover layer 50 to the conductive layer 60 and attaches the snap 46 to the conductive layer 60. A small aperture 48 is provided in the cover material 50. An aperture 52 is also provided in the double sided conductive tape 54 and aligned with the small aperture 48 in the cover material 50. The top portion 58 of snap 46 is assembled through the apertures 48, 52 so that the flange 56 of the snap 46 contacts the conductive tape 54. The top portion 58 of the snap 46 is exposed through the top (proximal) surface of the snap electrode through the apertures 48, 52, allowing for connection to a lead wire (not shown) to the electrode.

In each of the above embodiments, electrical current can flow from the stimulating device through the lead wires, to the top snap (if used) to the bottom snap and the conductive tape, to the conductive medium, to the gel and then finally to the subject's skin.

In the illustrative embodiments, the conductive top snap can be made from metal and the conductive bottom snap can be made from metal or plastic with a conductive layer deposited thereon. The cover layer can be made from a non-conductive material such as polypropylenes, polyethylene, polyurethane, foam, spun poly, tricot or other flexible material as is known in the art and typically includes a pressure sensitive adhesive disposed on its distal surface. The conductive tape is double sided in that it includes a top (proximal) surface and bottom (distal) surface each of which include a conductive adhesive such as conductive pressure sensitive adhesive disposed thereon.

The top snap is usually made from metal such as stainless steel or nickel plated brass. The bottom snap can be made from metal, plastic with a conductive coating or other conductive materials such as plastic loaded with carbon. As described hereinbefore with respect to FIG. 5, in certain embodiments only a bottom snap is used and no top snap is necessary.

The conductive layer 60 (FIG. 5) can be made from aluminum, tin or other metal as well as many different constructions of conductive plastic film such as, but not limited to, plain conductive film, or conductive film coated with a more conductive layer such as aluminum, silver, or silver chloride to one side or the other of the film.

Figure 6:
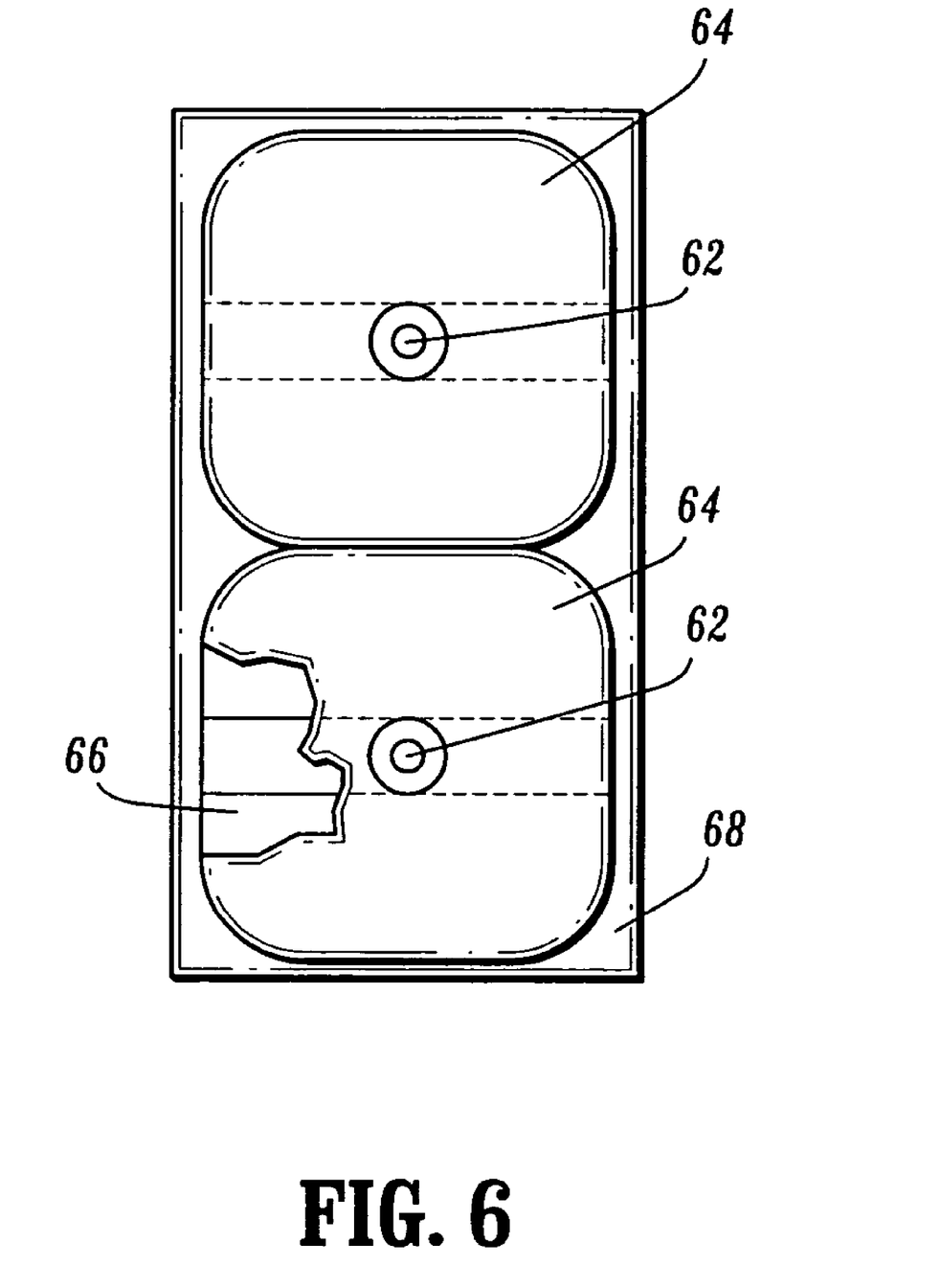
FIG. 6 is a top view of a pair of co-fabricated snap electrodes according to an illustrative embodiment of the invention.

A top view of a snap electrode according to the several embodiments of the present invention is shown in FIG. 6 in which a pair of snap electrodes are shown. A snap 62 extends proximally from the cover layer 64 for connection to a lead wire (not shown). A section of the cover layer 64 is cut away in one of the electrodes illustrated in FIG. 6 to show the conductive layer 66 below the cover layer 64 and substantially coextensive therewith. In each of the illustrative embodiments, a conductive gel can be applied to the bottom surface of the conductive layer to improve electrical contact with an area of a subject's skin. A removable release layer 68 is assembled on the bottom side to protect the gel during shipping and storage. It should be understood by persons skilled in the art that a number of electrodes can be fabricated together for shipping and storage with perforations in one or more of the cover layer 64, conductive layer 66 or release liner 68 for separation before use. It should also be understood by persons skilled in the art that snap electrodes according to the present disclosure can be fabricated in a variety of shapes and sizes.

Figure 7:
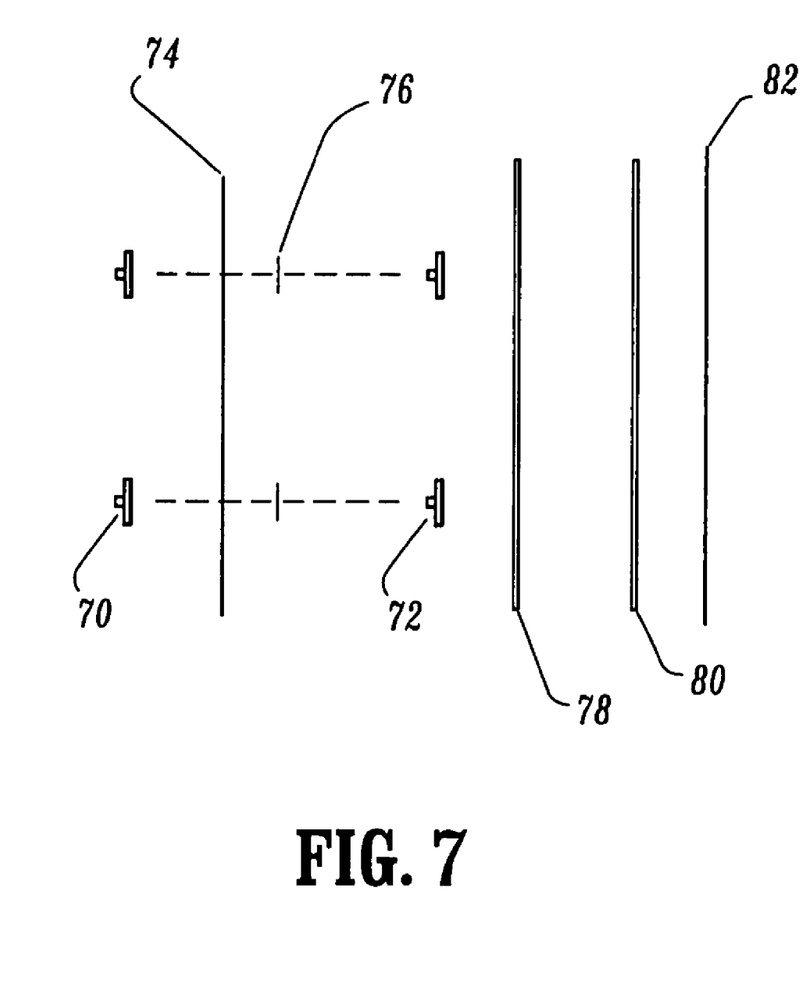
FIG. 7 is an exploded side view of a pair of co-fabricated snap electrodes according to an illustrative embodiment of the invention.

With reference to FIG. 7, an exploded side view of an illustrative embodiment of the invention including two electrodes fabricated together is shown. Each electrode includes a top snap 70 a bottom snap 72 with a cover layer 74 and a piece of conductive tape 76 disposed between the top snap 70 and bottom snap 72. The conductive layer 78 is assembled to the distal side of the cover layer snap and substantially coextensive therewith. A layer of conductive gel 80 is provided on the distal surface of the conductive layer 78. The conductive gel 80 can be made from a conductive adhesive such as one of many different hydrogels known to persons having ordinary skill in the art. A release liner 82 is disposed over the conductive gel 80 to protect the gel 80 during shipping and handling. The release liner 82 can be made from a film or paper substrate having a silicone coating on one or both sides. The release liner 82 is removed prior to installing the electrode against a subject's skin.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. An electrode comprising:
   a conductive layer having a proximal surface and a distal surface;
   a cover layer having a proximal surface and distal surface disposed over said conductive layer and substantially coextensive therewith;
   conductive tape disposed between said cover layer and said conductive layer and in electrical contact with said conductive layer; and
   at least one conductive snap in electrical contact with said conductive tape,
   wherein said at least one snap comprises a conductive bottom snap disposed between
   said conductive tape and said conductive layer and wherein said conductive tape has a proximal surface with a conductive adhesive disposed thereon and a distal surface with a conductive adhesive disposed thereon.

2. The electrode according to claim 1, wherein said conductive bottom snap includes a top portion that extends through said cover layer.

3. The electrode according to claim 1, wherein said conductive tape includes an aperture aligned with said bottom snap and wherein said cover layer includes an aperture aligned with said bottom snap such that said bottom snap is accessible for attachment of a lead wire through said cover layer.

4. The electrode according to claim 3, wherein said bottom snap includes a top portion which extends through said aperture in said cover layer.

5. The electrode according to claim 1, wherein said at least one conductive snap further comprises:
   a conductive top snap disposed on said proximal surface of said cover layer and mechanically engaged with said bottom snap; and wherein said conductive tape is disposed between said bottom snap and said top snap.

6. The electrode according to claim 5, wherein a portion of said conductive tape is pinched between mating portions of said conductive top snap and said bottom snap.

7. The electrode according to claim 5, wherein said cover layer includes an aperture aligned with said bottom snap.

8. The snap electrode according to claim 1, wherein said conductive tape includes an aperture aligned with said bottom snap.

9. The electrode according to claim 1, wherein said cover layer has a conductive adhesive disposed on its distal surface.

10. The electrode according to claim 1, comprising a conductive gel layer disposed on said distal surface of said conductive layer.

11. The electrode according to claim 10, further comprising a release layer covering said gel layer such that said gel layer is disposed between said conductive layer and said release layer.

12. The snap electrode according to claim 1, wherein said at least one snap is made from one of stainless steel or nickel plated brass.

13. The snap electrode according to claim 1, wherein said cover layer is made from one of foam, spun poly, tricot, polypropylene, polyethylene, or polyurethane and includes a pressure sensitive adhesive on its distal surface.

14. The snap electrode according to claim 1, wherein said conductive layer is made from one of aluminum, tin, plain conductive film, conductive film coated with an aluminum layer, conductive film coated with a silver layer, or conductive film coated with a silver chloride layer.

15. The snap electrode according to claim 1, wherein said at least one snap is not viewable through said distal surface of said conductive layer.

16. A snap electrode comprising:
    a conductive layer having a proximal surface and a distal surface;
    a cover layer having a proximal surface and distal surface disposed over said conductive layer and substantially coextensive therewith and having a conductive adhesive disposed on said distal surface;
    conductive tape disposed between said cover layer and said conductive layer wherein said conductive tape is in electrical contact with said conductive layer;
    a bottom snap disposed between said conductive tape and said conductive layer;
    a conductive top snap disposed on said proximal surface of said cover layer and mechanically engaged with said bottom snap, wherein said conductive tape is disposed, between said bottom snap and said top snap;
    a conductive gel layer disposed on said distal surface of said conductive layer; and
    a release layer covering said gel layer that said gel layer is disposed between said conductive layer and said release layer.

17. The snap electrode according to claim 16 wherein said conductive tape includes a proximal surface with conductive adhesive disposed thereon.

18. The snap electrode according to claim 16 wherein said conductive tape includes a distal surface with conductive adhesive disposed thereon.

* * * * *